US011174353B2

United States Patent
Old et al.

(10) Patent No.: US 11,174,353 B2
(45) Date of Patent: Nov. 16, 2021

(54) LINKERS FOR PROTEIN INTERACTION PROFILING AND METHODS OF MAKING AND USING THE SAME

(71) Applicant: THE REGENTS OF THE UNIVERSITY OF COLORADO, Denver, CO (US)

(72) Inventors: William Old, Denver, CO (US); Douglas A. Chapnick, Boulder, CO (US); Tristan D. McClure-Begley, Lafayette, CO (US); Tao Gong, Superior, CO (US); Brady Worrell, Boulder, CO (US); Christopher C. Ebmeier, Arvada, CO (US); Christopher Bowman, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 150 days.

(21) Appl. No.: 16/293,191

(22) Filed: Mar. 5, 2019

(65) Prior Publication Data

US 2019/0256667 A1    Aug. 22, 2019

Related U.S. Application Data

(62) Division of application No. 15/518,174, filed as application No. PCT/US2015/054965 on Oct. 9, 2015, now abandoned.

(60) Provisional application No. 62/061,973, filed on Oct. 9, 2014.

(51) Int. Cl.
  *C08H 1/00* (2006.01)
  *G01N 33/68* (2006.01)
  *C08K 5/10* (2006.01)

(52) U.S. Cl.
  CPC .................. *C08H 1/00* (2013.01); *C08K 5/10* (2013.01); *G01N 33/6848* (2013.01)

(58) Field of Classification Search
  None
  See application file for complete search history.

(56) References Cited

U.S. PATENT DOCUMENTS

| | | | |
|---|---|---|---|
| 3,082,245 | A | 3/1963 | Miller |
| 3,894,928 | A | 7/1975 | Kagiya et al. |
| 8,778,626 | B2 | 7/2014 | Sohn et al. |
| 2006/0094121 | A1 | 5/2006 | Reid et al. |
| 2007/0140967 | A1 | 6/2007 | Wood et al. |
| 2009/0130769 | A1 | 5/2009 | de Jong et al. |
| 2012/0269798 | A1 | 10/2012 | Reddien et al. |

(Continued)

FOREIGN PATENT DOCUMENTS

JP    2006-266708    * 10/2006 ........... G01N 33/547

OTHER PUBLICATIONS

Grove, G et al. Myocardial Matrix-Polyethylene Glycol Hybrid Hydrogels for Tissue Engineering, Nanotechnology, 25(1) (Year: 2014).*

(Continued)

*Primary Examiner* — Xiaoyun R Xu
(74) *Attorney, Agent, or Firm* — Sheridan Ross P.C.

(57) ABSTRACT

Crosslinking compounds for effective and efficient crosslinking and identification of intermolecular and intramolecular interactions of proteins, peptides and nucleic acids.

19 Claims, 7 Drawing Sheets

(56) References Cited

U.S. PATENT DOCUMENTS

2014/0141486 A1   5/2014   Jain et al.
2017/0321016 A1   11/2017  Old et al.

OTHER PUBLICATIONS

Baskin et al., "Copper-free click chemistry for dynamic in vivo imaging," PNAS, 2007, vol. 104(43), pp. 16793-16797.
Brittain et al., "Enrichment and analysis of peptide subsets using fluorous affinity tags and mass spectrometry," Nature Biotechnology, 2005, vol. 23, pp. 463-468.
Hermanson, "Introduction to Cross-linking and Photoactivatable Reagents," The Molecular Probes Handbook, 11th Edition, Chapters, Section 5.1, Thermo Fisher Scientific, 2008, 3 pages.
Herzog et al., "Structural Probing of a Protein Phosphatase 2A Network by Chemical Cross-Linking and Mass Spectrometry," Science, 2012, vol. 337, pp. 1348-1352, 6 pages.
Jewett et al., "Cu-free click cycloaddition reactions in chemical biology," Chemical Society Review, 2010, vol. 39(4), pp. 1272-1279, 29 pages.
Lu et al. "Ionic Reagent for Controlling the Gas-Phase Fragmentation Reactions of Cross-Linked Peptides," Analytical Chemistry, 2008, vol. 80, pp. 9279-9287.
Marks et al., "Desensitization of Nicotine-Stimulated 86Rb+ Efflux from Mouse Brain Synaptosomes," Journal of Neurochemistry, 1994, vol. 63(6), pp. 2125-2135.
Rostovtsev et al., "A Stepwise Huisgen Cycloaddition Process: Copper(I)-Catalyzed Regioselective 'Ligation' of Azides and Terminal Alkynes," Angewandte Chemie—International Edition, 2002, vol. 41(14), pp. 2596-2599.
Shukla et al., "Visualization of arrestin recruitment by a G-protein-coupled receptor," Nature, 2014, vol. 512(7513), pp. 218-222, 31 pages.
Srinivassan, "Nicotine up-regulates $\alpha 4\beta 2$ nicotinic receptors and ER exit sites via stoichiometry-dependent chaperoning," Journal of General Physiology, 2010, vol. 137(1), pp. 59-79.
Szychowski et al., "Cleavable Biotin Probes for Labeling of Biomolecules via Azide-Alkyne Cycloaddition," Journal of the American Chemical Society, 2010, vol. 132(51), pp. 18351-18360, 25 pages.
Tornoe et al., "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem., 2002, vol. 67, pp. 3057-3064.
Zhou et al., "Human $\alpha 4\beta 2$ Acetylcholine Receptors Formed from Linked Subunits," Journal of Neuroscience, 2003, vol. 23(27), p. 9004-9015.
International Search Report and Written Opinion for International (PCT) Patent Application No. PCT/US15/54965, dated Jan. 5, 2016, 6 pages.
International Preliminary Report on Patentability for International (PCT) Patent Application No. PCT/US15/54965, dated Apr. 20, 2017, 5 pages.
Official Action for U.S. Appl. No. 15/518,174, dated Oct. 5, 2018 11 pages.

* cited by examiner

LINKERS FOR PROTEIN INTERACTION PROFILING AND METHODS OF MAKING AND USING THE SAME

CROSS REFERENCE TO RELATED APPLICATION

This application is a divisional of U.S. patent application Ser. No. 15/518,174, filed Apr. 10, 2017, which is a national stage application under 35 U.S.C. 371 of PCT Application No. PCT/US2015/054965, having an international filing date of Oct. 9, 2015, which designated the United States, which PCT application claimed the benefit of U.S. Application Ser. No. 62/061,973, filed on Oct. 9, 2014. Each of these applications are incorporated herein by reference in their entirety.

STATEMENT REGARDING FEDERALLY SPONSORED RESEARCH

This invention was made with government support under grant number CHE1214109, awarded by the National Science Foundation, and grant number W911NF-14-2-0019, awarded by the U.S. Army Research Office. The U.S. government has certain rights in the invention.

TECHNICAL FIELD

This application resides in the field of cross-linkers and methods of identifying peptide and protein interactions using the cross-linkers.

BACKGROUND

Protein interactions represent the foundation of nearly every aspect of cell signaling. The post-translational modification of proteins, cytoskeletal rearrangements, and stimulated chemical communications between cells and tissues are all the direct result of proteins coming together in tightly defined and orchestrated geometry resulting in a critical event. Yet, the ability to observe the consequences of such interactions has radically outpaced the technology development required to actually capture all the interactions themselves. For example, the observed changes in phosphorylation states of proteins are often interrogated with pharmacological manipulations of classes of protein kinases and phosphatases, which produce indirect evidence of the relevant interaction by virtue of its loss coinciding with the measured loss in the activity of a class of proteins. More information could be gained, however, if these interactions could be directly trapped and changes in their frequency and/or geometry observed according to a relevant state in a cell.

Popular techniques to monitor protein changes are high resolution methods such as x-ray crystallography and nuclear magnetic resonance spectroscopy (NMR). However, these techniques have limitations. They required large amounts (10-100 mg) of very pure protein. NMR is also limited by the size of the protein (~40 kD limit), while crystallography requires the formation of a crystal, which is not always possible and does not mimic solution behavior, as the crystal is the thermodynamic minima of the ensemble. Chemical cross-linking is another technique that has recently been employed to study protein-protein interactions. This technique has become more prevalent with the coupling of crosslinking methods with mass spectrometry. These techniques chemically cross-link proteins through a reaction with a cross-linker reagent, which creates a stable, covalent linkage between specific amino acids of the protein. The cross-linker imposes a distance constraint on the location of protein functional groups capturing a snapshot of their interaction. This technique can be used intramolecularly to gain insight into the 3D structure of a single protein as well. Some of the major advantages to cross-linking are: 1) it is applicable to low (micromolar) concentrations of protein; 2) it captures a snapshot of the protein in its native/dynamic conditions; and 3) it can be easily coupled to mass spectrometry for detection of cross-linked products and identification of cross-link site. Chemical cross-linkers have been widely employed in analysis of three-dimensional protein structures and protein-protein interactions (PPIs). Formaldehyde and glutaraldehyde are often employed for their rapid reaction rates and extensive degree of protein crosslinking, thus, preserving cells and tissues for histological examinations. The most widely employed protein cross-linkers use N-hydroxysuccinimide (NHS) esters, which can undergo rapid $S_N2$-type reactions with primary amines. Unfortunately, such activated ester probes are susceptible to hydrolysis by water, thus compromising their utility for in vivo crosslinking. Carbodiimide reagents, such as 1-Ethyl-3-[3-dimethylaminopropyl]carbodiimide (EDC), activate carboxylic acids and generate new peptide bonds with adjacent amine residues, resulting in zero-length protein coupling. When photoactivateable groups, such as diazirines and benzophenones, are employed as part of heterofunctional protein crosslinkers, reactive carbenes can easily be liberated which will readily add to any adjacent residue or abscond hydroxyl groups from water molecules to form alcohols. Again, such chemical probes, although commonly employed for the covalent crosslinking of proteins, are highly susceptible to deleterious non-productive reactions with the aqueous environment. Recently, technological advances in hybrid high-resolution mass spectrometry instrumentation and computational algorithms have allowed for the detection of binding partners and specific contacting residues with increased sensitivity. For example, these techniques have been used to explore the regulatory interactions of a protein phosphatase (PP2A; Herzog et al, Science 337(6100):1348-52; PMID 22984071), the docking geometry of β-arrestin with β-adrenergic g-protein coupled receptors (GPCRs) (Shukla et al, Nature 512(7513):218-22; PMID 25043026), in which relatively high-affinity, yet transient interactions between proteins were successfully captured with chemical crosslinkers.

With each of the listed crosslinking chemistries (vide supra), inherent difficulties arise in terms of the conditions used to maximize the production of informative crosslinks, and the physiologically relevant states of cells and tissues. For example, the use of carbodiimides requires proteins to be accessible to a charged molecule, and cannot, therefore, be employed with much success in the linking of proteins within selectively permeable membranes. NHS-esters are prone to spontaneous hydrolysis, resulting in decreased efficacy and often unpredictable performance from one experiment to the next. All currently commercially-available protein crosslinkers designed for use with mass spectrometry-based protein identification and profiling are employed to optimal effect at pH values that lay outside those typically encountered in native cellular compartments, and are therefore somewhat limited in the nature and diversity of the interactions they can trap. For this reason, investigation of protein interactions in vivo typically relies on protein complex immunoprecipitation ("pull-down" assays) to recover interacting protein or peptide partners. Alternatively, affinity tags can be used in genes encoding target proteins to permit efficient purification from cell lysates. However, many important protein interactions are weak interactions that are not strong enough to be identified by these methods. Thus, there is a strong desire for chemical cross-linking compounds and methods of using the compounds, particularly in vivo, to freeze protein interactions by forming covalent bonds, allowing sample analysis, optionally combined with other protein purification techniques in an aqueous environment.

SUMMARY

The present disclosure describes the conception, synthesis, and application of a novel protein crosslinking chemistry, based on the use of electron-deficient alkyne/propiolate Michael acceptors which react selectively with amine- and sulfhydryl-bearing amino acids. The cross-linker compounds are useful in methods for preparing one or more cross-linked biomolecules, biomolecular complexes of two or more biomolecules, and fragments from such cross-linked biomolecules and/or biomolecular complexes, as well as methods for identifying cross-links in such cross-linked biomolecules and/or biomolecular complexes.

One aspect of the disclosure is a crosslinker compound having the chemical structure:

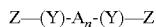

Z—(Y)-$A_n$-(Y)—Z wherein:
n=1-5;
A is an organic compound that may be optionally substituted with one or more collision-induced dissociation groups, and one or more affinity handles. Each A can act independently or as a Q or L, wherein Q is an affinity handle and L is a molecular label.

Each A may be joined to Z through one or more optional linking group Y, wherein each Y is an organic compound of $C_{1-10}$, optionally substituted with one or more heteroatoms selected from O, N, S, or P and one or more collision-induced dissociation groups, and one or more affinity handles.

The Michael acceptor (Z) of these compounds may include at least one compound selected from propiolate, propiolamide/propargylamide, ynone, ynethiolate, acrylate, and vinylsulfone. In certain embodiments, Z is at least one of:

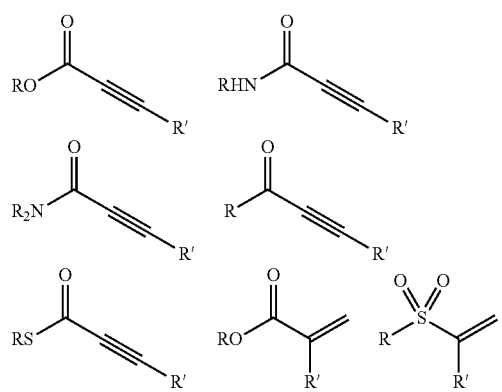

The affinity handles (Q) may include at least one compound selected from biotin, streptavidin, PEG, antibody, organic azide, or non-Michael accepting alkyne.

The molecular labels (L) may include at least one compound selected from phosphors, radioactive atoms, fluorescent dyes, electron-dense reagents, enzymes, biotin, digoxigenin, haptens or proteins made detectable by incorporating a metal, radiolabel or phosphor into the peptide, hydrolases, phosphatases, esterases and glycosidases, or oxidotases, peroxidases, fluorescein and its derivatives, rhodamine and its derivatives, dansyl, umbelliferone, luciferin, and 2,3-dihydrophthalazinediones, The linking group (Y) may be chosen to have a molecular length of between 1 angstrom and 50 angstroms, preferably between about 5 angstroms and about 20 angstroms, most preferably about 12 angstroms.

In some embodiments, the crosslinking compound is a dipropiolate. In certain embodiments, the crosslinking compound is at least one of butane-1,4-diyldipropiolate; oxybis(ethane-2,1-diyl) dipropiolate; and di(cylcohexyl-2,1-diyl) dipropriolate.

Crosslinking Compound:

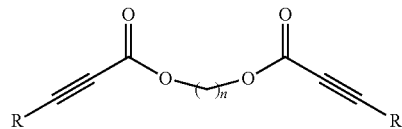

SPECIFIC EXAMPLES

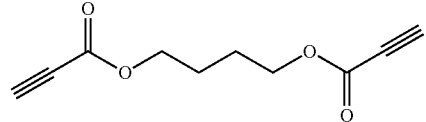

butane-1,4-diyl dipropiolate

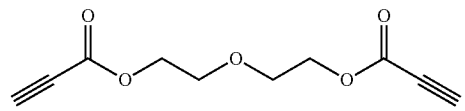

oxybis(ethane-2,1-diyl) dipropiolate

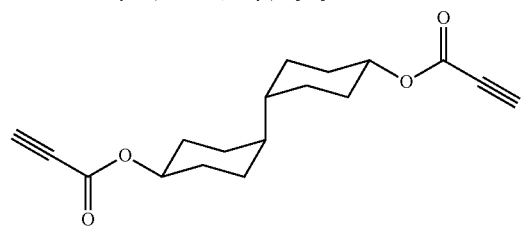

di(cylcohexyl-2,1-diyl) dipropriolate

Another aspect of the invention provides methods of crosslinking at least one protein or peptide, which include mixing a sample containing the at least one protein or peptide with a crosslinker compound of this disclosure to form a crosslinked protein or peptide; fragmenting the crosslinked protein or peptide to form fragmented peptides; introducing the fragmented peptides into a mass spectrometer and detecting a mass-to-charge ratio of the fragmented peptides.

In these methods, the mixing step may be conducted at pH between pH 5 and pH 10, preferably between pH 6 to pH 9, and more preferably between pH 6 to pH 8. In certain embodiments, the mixing step may be conducted at a physiological pH of about 7.4.

In these methods, the fragmenting step may include digesting the cross-linked sample using a protease.

These methods may further comprise using the detected mass-to-charge ratio of the fragmented peptides to determine an amino acid sequence associated with the fragmented peptides.

These methods may further comprise using the detected mass-to-charge ratio of the fragmented peptides to identify intermolecular and intramolecular protein interactions in a sample comprising the at least one protein or peptide.

Figure 3:
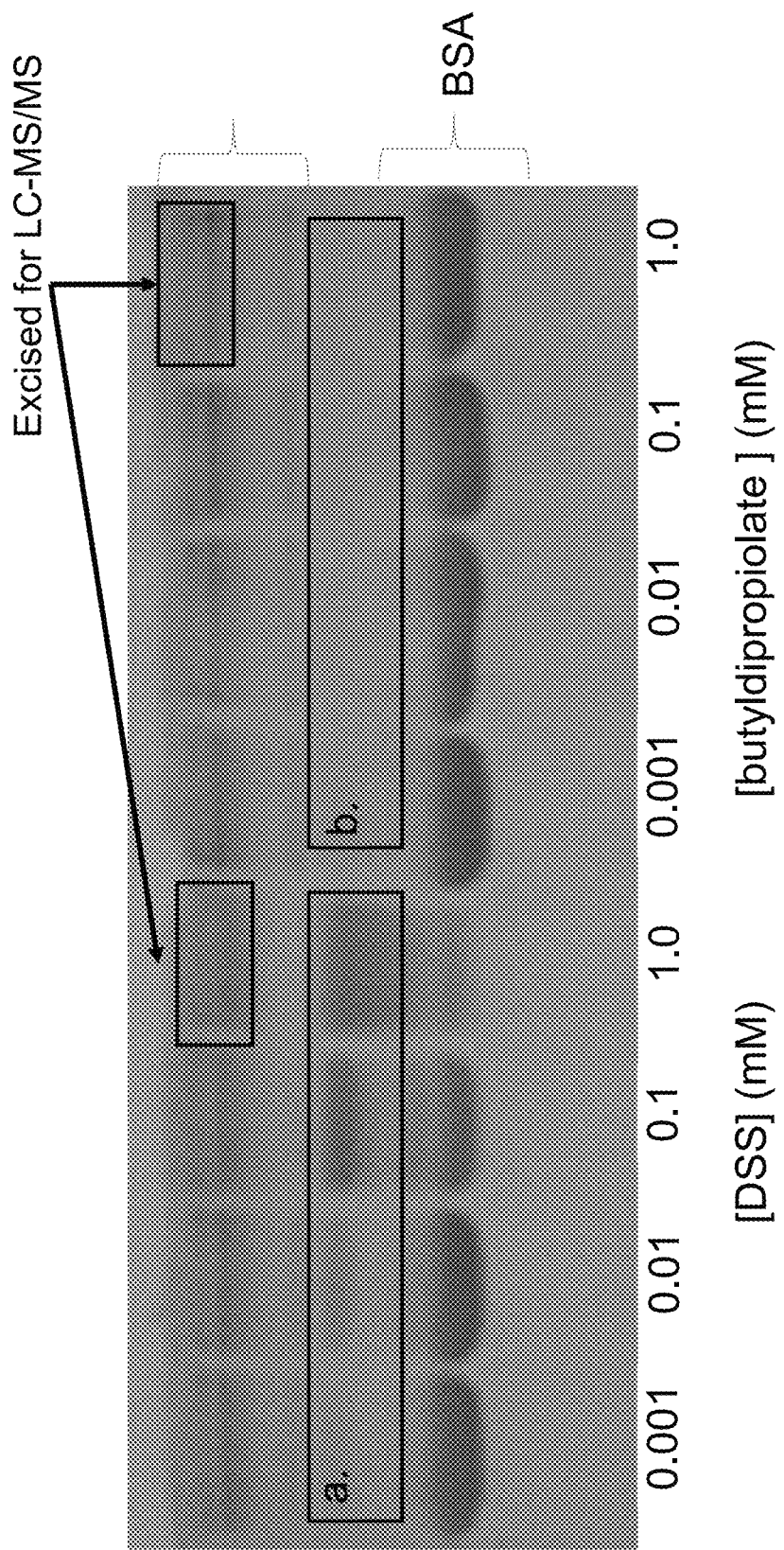
FIG. 3 is a coomassie stained polyacrylamide gel showing the tendency of disuccinimidyl suberate to generate nonspecific protein crosslinks between bovine serum albumin and yeast ADH, and the relative lack of nonspecific crosslinks produced by butyldipropriolate.

Tables 1a and 1b are tabulations of protein:protein crosslinks identified by LC-MS/MS analysis of proteins present in gel bands excised from the polyacrylamide gel pictured in FIG. 3.

Figure 4:
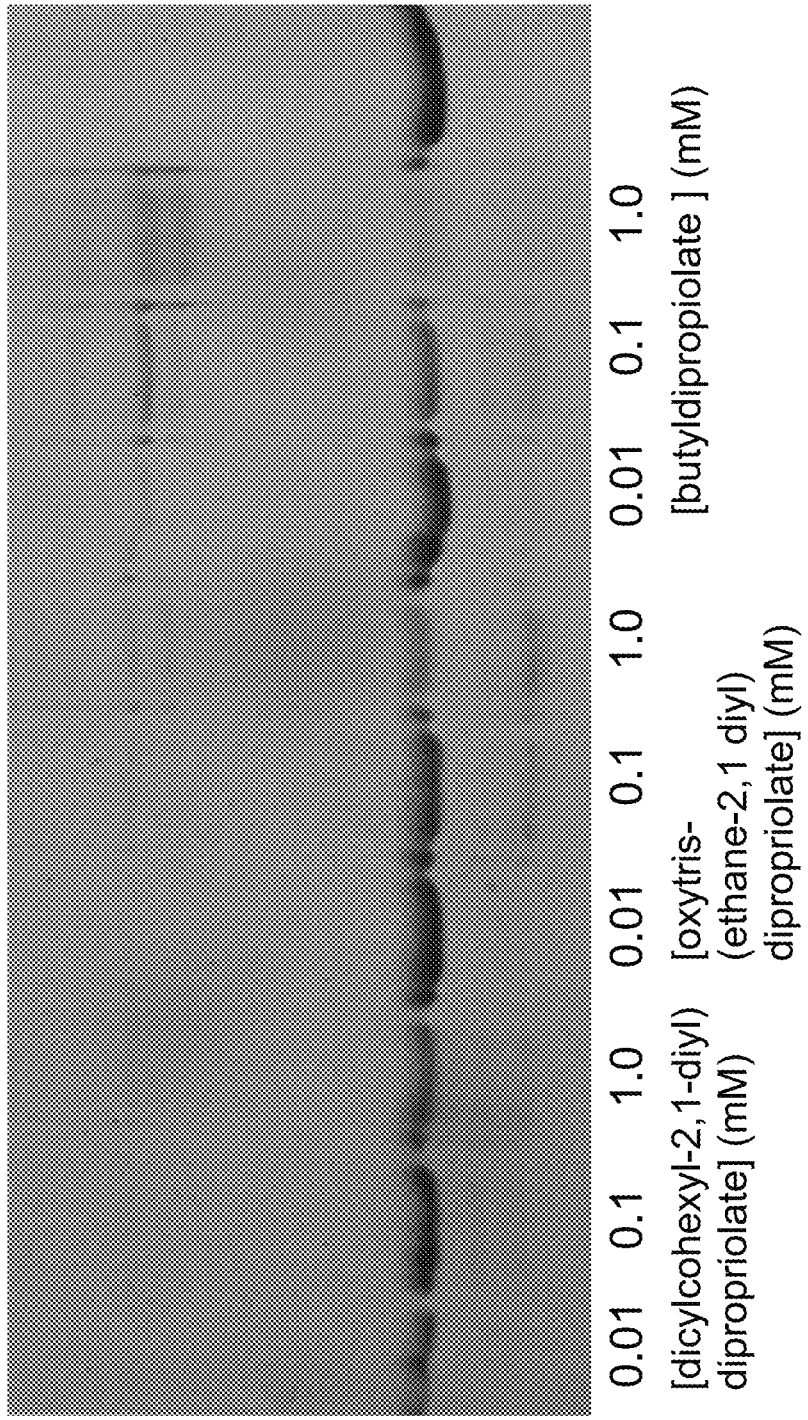

FIG. 4 is a coomassie stained polyacrylamide gel showing characteristic electrophoretic mobility shifts of yeast ADH following crosslinking by butyldipropriolate, oxybis(ethane-2,1-diyl) dipropiolate, and di(cylcohexyl-2,1-diyl) dipropriolate.

Figure 5:
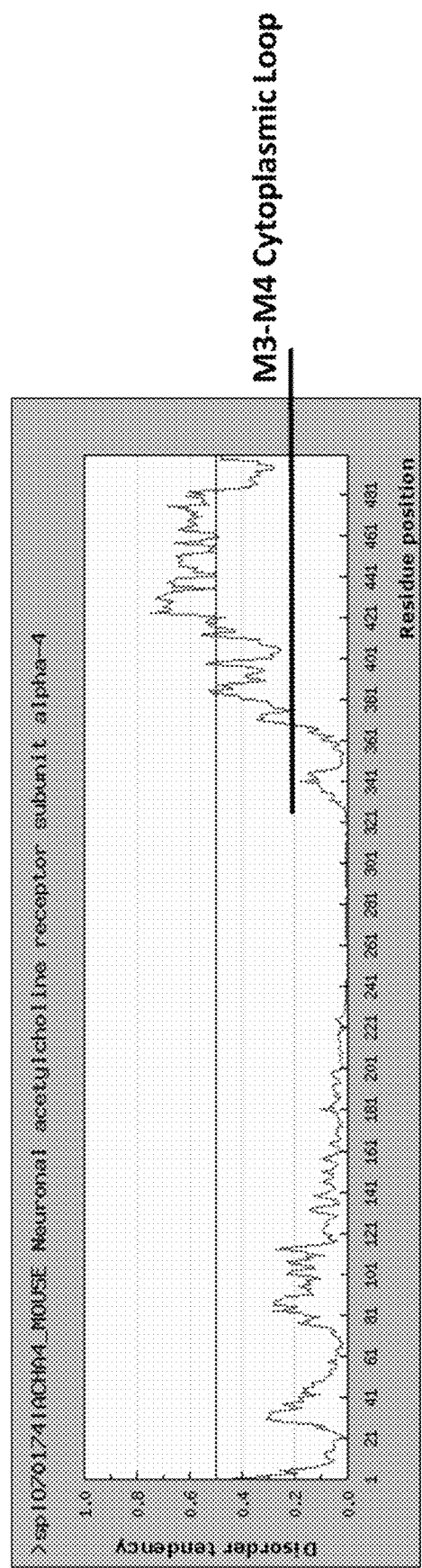

FIG. 5 is an IUPRED depiction of intrinsic protein disorder in the M3-M4 subunit of the mouse α4 nicotinic acetylcholine receptor subunit.

Tables 2a and 2b are tablulations of inter-subunit crosslinks identified for α4β2 nicotinic receptors that map to the extracellular and intracellular domains under control cell culture conditions and following 24 hour incubation with 1 µM nicotine to induce desensitized receptor conformations.

DETAILED DESCRIPTION

Aspects of the present invention provide crosslinking compounds having electron-deficient alkyne protein-reactive groups, which crosslink proteins/peptides through direct coupling of amino groups on lysine residues, similar to NHS-ester based crosslinkers, but with superior performance across a physiologically relevant range of pH and with substantially reduced nonspecific protein conjugation. These crosslinking compounds are useful for the investigation of protein-protein interactions (PPIs), three-dimensional protein structures, as well as protein-nucleic acid (DNA or RNA) interactions, in addition to being useful as protein conjugation reagents. Analysis of these structures and interactions can lead to identification of ligand binding sites on proteins and associated conformational sites that provide insight into many applications, such as molecular docking, de novo drug design and structural identification and comparison of functional sites.

These crosslinking compounds afford distinct advantages over other currently available cross-linkers. For example, the inventors have demonstrated that Michael acceptor protein-reactive groups are less dependent on alkaline pH than amine-specific crosslinking reagents based on N-hydroxysuccinimide ester (NHS ester) crosslinkers (such as disuccinimidyl suberate; DSS) and, therefore, are more likely to preserve relevant protein:protein interactions across cellular compartments and organelle environments that may be selected against profiling with other commercially available reagents.

Crosslinking Compounds

The crosslinking compounds of this disclosure include compounds having the chemical structure:

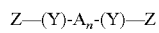

$$Z-(Y)-A_n-(Y)-Z$$

wherein n is an integer between 1 and 5. A is an atom or compound which serves as a central atom to which additional reactive group(s) and/or affinity group(s), as defined below, can be attached. In certain embodiments, A is phosphorus (P), sulfur (S), nitrogen (N), or oxygen (O).

Each Y is an optional $C_{1-10}$ alkyl or aromatic spacer to attach reactive group(s) and/or affinity group(s), as defined below. Such substituted $C_{1-10}$ alkyl may include cycloalkyl, such as pentane or hexane, as well as heteroalkyl and heterocycloalkyl, including common organic heteroatoms, such as phosphorus (P), sulfur (S), nitrogen (N), or oxygen (O). Aromatic spacers, including benzene, extended aromatic systems, or heterocycles including common organic heteroatoms as listed above are also covered by this claim.

Each A can act independently or as a Q or L, when Q is an affinity handle and L is a molecular label.

The Michael acceptor (Z) of these compounds is a chemical moiety that is capable of conjugating to a protein, peptide and/or a nucleic acid. Z is an electrophile that forms a covalent bond with a donor moiety (i.e., a nucleophile) in the target compound via a Michael reaction. In certain embodiments, the Michael acceptor electrophile (Z) is an electron-deficient alkyne.

Thus, the donor moiety present in the target compound is a nucleophile that reacts with the Michael acceptor (Z) via a Michael reaction to form a covalent bond between the crosslinking compound and the target compound. Examples of typical target compounds include proteins, peptides or nucleic acids (DNA or RNA) (collectively "biomolecules") that are of interest for crosslinking via the methods of this disclosure). The Michael acceptor (Z) often reacts with lysine and free cysteine moieties present in proteins or peptides, for example accessible ε-amino groups on lysine residues.

As multiple, independent moieties (Z) may be present in the crosslinking compounds of this disclosure, these crosslinking compounds are capable of simultaneously conjugating to a protein or peptide and a nucleic acid. For example, Michael acceptors (Z) that are capable of conjugating to proteins or peptides react with a specific amino acid of the peptide or protein. Similarly, Michael acceptors (Z) that are capable of conjugating to a nucleic acid molecule (such as DNA or RNA) react with at least one specific nucleic acid base or other chemical functionality in the nucleic acid molecule.

In some embodiments, each Michael acceptor (Z) is/are the same, thereby rendering the cross-linker compound homobifunctional, homotrifunctional, etc. That is, when each Michael acceptor (Z) is the same, the crosslinker makes two of the same conjugations to the peptide(s), protein(s) or nucleic acid molecules to be cross-linked.

In other embodiments, each Michael acceptor (Z) is/are different, i.e., the crosslinker is heterobifunctional, heterotrifunctional, etc., and makes two different conjugations to the peptides(s), protein(s) or nucleic acid molecules to be cross-linked.

In some embodiments, when each Michael acceptor (Z) is/are different, at least one Z may be an electrophilic Michael acceptor group that is capable of conjugating to an amino acid of a protein or peptide, and another Z is capable of conjugating to a nucleic acid base, or other chemical functionality of a nucleic acid molecule. In this way, a heterobifunctional crosslinker having a Michael acceptor (Z) capable of conjugating to an amino acid (e.g. an amine-reactive group) and a Michael acceptor (Z) capable of conjugating to a nucleic acid base (e.g. a thymine-reactive group), is capable of conjugating to both a protein or peptide and a nucleic acid molecule.

Preferred embodiments of crosslinking compounds of this disclosure include a Michael acceptor (Z) that include at least one compound selected from propiolate, propiolamide/propargylammide, ynone, ynethiolate, acrylate, and vinylsulfone. These chemical moieties are readily understood by those of skill in the art familiar with organic chemistry and Michael reactions and are readily available as starting materials for synthesis of these crosslinking molecules. Other Michael acceptor (Z) groups are available that would be suitable for alternative embodiments of the subject matter of this disclosure. Those of skill in the art will understand that any suitable Michael acceptor, now known or hereafter developed, may be used in forming the cross-linking compounds described herein.

Affinity handle (Q) refers to a chemical moiety that may be attached to the crosslinker compounds of this disclosure to facilitate enrichment of crosslinker-modified species from a sample that may include mixtures of unmodified compounds (i.e., non-crosslinked compounds) as well as other biological or non-biological molecules present in a sample containing biomolecules of interest. The affinity handle(s) enrich the cross-linked molecule(s) by precipitation or separation of the "handle" moiety. For example, an affinity handle may be precipitated by its corresponding binding moiety (e.g., biotin is precipitated by avidin; histidine is precipitated by nickel, and an antibody is precipitated by its antigen). In related embodiments, the affinity handle (Q) may be absent from the cross-linking compounds of this disclosure but a target protein may naturally express, or be engineered to express, an affinity handle and the crosslinked protein may be enriched using that affinity handle.

These affinity handles are readily understood by those of skill in the art familiar with organic chemistry and protein and peptide purification methods and are available as starting materials or in kits from various manufacturers for synthesis of these crosslinking molecules. Examples may include, but are not limited to, amino acid sequences (e.g., polyhistidine or antibody fragments), small-molecules (e.g. biotin), or nucleic acid sequences (e.g., DNA or RNA). Exemplary affinity handles include at least one compound selected from biotin, streptavidin, PEG, antibodies, or similar tags. Those of skill in the art will understand suitable affinity groups that can be used to further isolate or purify the crosslinked compounds formed in a sample or composition.

Molecular labels (L) are one or more chemical entities that render the crosslinking compounds of this disclosure (and therefore crosslinked compounds in a sample or composition) distinguishable by some physical means (e.g. by mass) because of the presence of the label. Non-limiting examples of molecular labels (L) may include at least one compound selected from phosphors, radioactive atoms, atomic isotopes, fluorescent dyes, electron-dense reagents, enzymes, biotin, digoxigenin, haptens or proteins made detectable by incorporating a metal, radiolabel or phosphor into the peptide, hydrolases, phosphatases, esterases and glycosidases, or oxidotases, peroxidases, fluorescein and its derivatives, rhodamine and its derivatives, dansyl, umbelliferone, luciferin, and 2,3-dihydrophthalazinediones. Exemplary isotopes that may be used as the molecular label (L) include, without limitation: carbon ($C^{12}$ and $C^{13}$), nitrogen (e.g., $N^{14}$ and $N^{15}$), sulfur (e.g., $S^{32}$ and $S^{34}$), oxygen (e.g., $O^{16}$, $O^{17}$ and $O^{18}$), bromine ($Br^{79}$ and $Br^{81}$), or chloride (e.g., $Cl^{35}$ and $Cl^{37}$).

Each A may be joined to Z through one or more optional linking group(s) (Y), wherein each Y is independently an organic compound of $C_{1-10}$, optionally substituted with one or more heteroatoms selected from O, N, S, or P. Each Y may independently include a cleavable linker portion that may include one or more cleavage sites, which may be cleaved by chemical cleavage agents, enzymatic cleavage agents, or both chemical cleavage agents and enzymatic cleavage agents. When present in the crosslinking compounds of this disclosure, the linking group(s) (Y), may be substituted or appended to include the functional affinity handles (Q) or molecular labels (L) in addition to one or more cleavage sites.

Additionally, these linking group(s) (Y) may include one or more collision-induced dissociation groups. Collision-induced dissociation groups may include signature ions (e.g., the precursors of signature ions) formed upon CID, particularly in CID/MS/MS methods. The presence of such CID groups may provide greater specificity in protein or peptide identification in the methods of this disclosure, compared to that of pure MS-based methods. Examples of such CID dissociation groups include fixed-charge sulfonium ion derivatives of the amino acids methionine and cysteine, which fragment exclusively via neutral loss of the side chain $CH_3SR$, where R is a substituted alkyl group.

The optional linking group (Y) may be chosen to have a molecular length of between about 1 angstrom and about 50 angstroms, preferably between about 5 angstroms and about 20 angstroms, more preferably about 12 angstroms.

In some embodiments, the crosslinking compound of this disclosure is a dipropiolate. In certain embodiments, the crosslinking compound is at least one of butane-1,4-diyl dipropiolate; oxybis(ethane-2,1-diyl) dipropiolate; and di(cylcohexyl-2,1-diyl) dipropriolate.

Methods of Cross-Linking and Analysis

Using the disclosed methods, a protein or a protein complex may be analyzed to elucidate protein structure or the interaction between proteins or protein complexes, when used in combination with mass spectrometry.

Various methods may be used to investigate the cross-linked biomolecules to evaluate the protein or nucleic acid molecules and their interactions. Essentially, crosslinkers are added into the interacting proteins and/or nucleic acids. The crosslinkers capture the interactions by forming covalent chemical bonds with accessible amino acid residue side chains on the biomolecules. The crosslinked biomolecules are enzymatically digested directly in solution or in gel bands after separation. By analyzing the digest on a mass spectrometer (that may include LC separation), the crosslinked molecules can be detected because they have modified mass due to the crosslinker. With MS/MS spectra and pre-knowledge of which amino acid side chains the crosslinker reacts with, the exact amino acid residues that are crosslinked are determined. This analysis step may be more efficiently completed with computer algorithms than with manual processing because of the numerous possibilities for crosslinking peptides and nucleic acids. Both commercial and customized computer programs are available for this purpose.

This analysis (based on the MS data) determines which residues in the biomolecules are crosslinked to each other. In the protein complex structure, these residues should be apart from each other at the distance of the length of the crosslinker used in the study. This spatial constraint information can be combined with mutation studies and structures from X-ray crystallography or NMR to further examine aspects of the binding interface. Additionally, computational docking structure data may provide additional insight into the interactions of the crosslinked biomolecules and/or confirm the results of this crosslinking-MS analysis.

Thus, in some embodiments, methods of crosslinking a biomolecule of this disclosure includes mixing a sample or composition having at least one protein, peptide or nucleic acid of interest with a crosslinker compound of this disclosure. The mixing may be conducted in vivo, in vitro, or in situ. A variety of samples may be analyzed for protein interactions. The samples are obtained from cell lysate or cell culture or a clinically relevant tissue or serum sample. In certain embodiments, one or more proteins are crosslinked inside substantially intact cells before isolation and subsequent analysis.

Suitable conditions for the crosslinking in the mixing step may include a pH in the physiological range of the protein, peptide or nucleic acid molecules of interest. Thus, the mixing step may be conducted at pH between pH 5 and pH 10, or between pH 6 to pH 9, or between pH 6 to pH 8. In certain embodiments, the mixing step may be conducted at a pH of about 7.4.

After mixing in order to generate a sample containing crosslinked molecules for MS analysis, the sample may be further processed or purified (for example gel electrophoresis, and subsequent enzymatic digestion/reduction of a crosslinked product), In certain embodiments, the cross-linked sample is digested with an enzymatic or chemical cleaving agent(s). This digestion may include the step of fragmenting the cross-linked biomolecules, biomolecular complexes or mixtures thereof. The fragments are digested to obtain cross-linked species from the cross-linked biomolecules or biomolecular complexes of sufficient small size for further analysis. Cross-linked fragments can be prepared by any method known in the art for cleaving large biomolecules into smaller fragments. Such fragmentation can be performed by chemical protein cleavage or treatment of proteins with proteolytic enzymes as to obtain smaller size fragments. Fragmentation using selective cleavage reagents results in fragments that are more easily identified than fragments obtained by a non-selective cleavage. Examples of specific chemical cleavage agents for proteins and peptides are CNBr, which cleaves proteins at methionine residues, and dilute acid at pH 2, which cleaves specifically at aspartate residues at high temperature, e.g. 108° C. Examples of specific proteases are trypsin, cleaving at lysine and arginine residues and Glu-C endoproteinase, cleaving at glutamate and, to a lesser extent, at aspartate residues. Efficient cleavage of cross-linked protein complexes can also be performed with pepsin, cleaving preferentially in hydrophobic segments with poor residue selectivity. In complex structures, identification of peptic peptides is more time-consuming than identification of peptides obtained by selective cleavage. Fragmentation can also be achieved by using a combination of two or more of such cleavage methods. For sequence specific cleavage of DNA in protein-DNA crosslinks, restriction enzymes can be employed. However, for cross-linked protein-DNA or protein-RNA complexes, non-specific nucleases, such as DNase I and the RNase α-sarcin, can be employed to decrease the size of the cross-linked nucleic acid moiety.

In order to purify or isolate the crosslinked biomolecule, the crosslinked complexes may be separated by, for example, liquid chromatography or gel electrophoresis. Additionally or alternatively, the crosslinked complexes including an affinity handle as part of the crosslinking compound may be precipitated, captured, or separated by capturing the affinity handle, thereby capturing the crosslinked complex or complex fragments. For example, a biotin affinity handle may be captured or enriched by avidin affinity chromatography. As would be understood by those of ordinary skill in the art, the complexity of the sample will determine the need to perform one or more of these additional purification steps. Also, when needed, those of ordinary skill in the art would be able to determine which purification steps to employ and how to employ them, based on the identity of a specific affinity handle within the crosslinking compound employed.

The crosslinked biomolecules, or fragments thereof, may be dissociated to form a dissociated sample. The dissociation process may be any suitable dissociation method including, but not limited to, collisions with an inert gas (known as collision-induced dissociation (CID or collisionally-activated dissociation (CAD); (ii) collisions with a surface (known as surface-induced dissociation or SID); (iii) interaction with photons (e.g. via a laser) resulting in photodissociation; (iv) thermal/black body infrared radiative dissociation (BIRD), and (v) interaction with an electron beam, resulting in electron-induced dissociation for singly charged cations (EID), electron-capture dissociation (ECD) for multiply charged cations, or combinations thereof.

The crosslinked biomolecules, or fragments thereof, may also be ionized by methods that may include, but are not limited to, electrospray ionization (ESI), matrix-assisted laser desorption ionization (MALDI), or fast atom bombardment (FAB). The ionized sample may subsequently be activated to fragment the ions of the ionized sample. In some embodiments, this activation (fragmentation) is carried out by collision induced dissociation (CID), electron transfer dissociation (ETD), pulsed Q dissociation (PQD), high energy C-trap dissociation (HCD) or CID-HCD. Tandem mass spectrometry (MS/MS) instrumentation allows for the implementation of ionization and fragmentation. In certain embodiments, the crosslinked biomolecules, or fragments are passed through a first mass resolving spectrometer to select precursor protein or peptide ions having a first desired mass-to-charge ratio; subjecting the precursor ions of the first mass to charge ratio to dissociation to form a product ion having a second mass-to-charge ratio and detecting the product ions.

Analysis of the mass-to-charge ratio results can efficiently and accurately determine the intramolecular and intermolecular (protein, peptide and/or nucleic acid) interactions associated with a crosslinked biomolecule. The methods of analysis of the present disclosure may be used for amino acid, peptide or protein identification, differential quantitation, analysis of post translational modification status, and analysis of cross-linking status or interaction of proteins.

Synthesis of Crosslinker Compounds

The synthesis of a crosslinker compound of this disclosure is carried out using known methods of organic synthesis, as described in the Examples and references cited herein. For example, The Molecular Probes Handbook, 11th Edition, Cross-linking and Photoactivatable Reagents, Chapter 5, Section 5.1 *Invitrogen Life Science*; and Bioconjugate Reagents, Bioconjugate Techniques, 2nd Edition, by Greg T. Hermanson, Published by Academic Press, Inc., 2008; Rostovtsev et al., *Angew. Chem.—Int. Edit.* 2002, 41, 2596; Tornoe et al., *J. Org. Chem.* 2002, 67, 3057; Baskin et al., *Proc. Natl. Acad. Sci. U.S.A.* 2007, 104, 16793; Jewett and Bertozzi, *Chem. Soc. Rev.,* 2010, 39, 1272, Szychowski et al., *J. Am. Chem. Soc.* 2010, 132, 18351 and Brittain et al., *Nat. Biotechnol.* 2005, 23, 463, all of which are incorporated herein. Chemists of ordinary skill in the art can modify the synthesis scheme based on the selection of variable groups in the crosslinking compounds of this disclosure.

The following Examples are presented for illustrative purposes only, and do not limit the scope or content of the present application.

EXAMPLES

Example 1 In Vitro Crosslinking

Figure 1A:
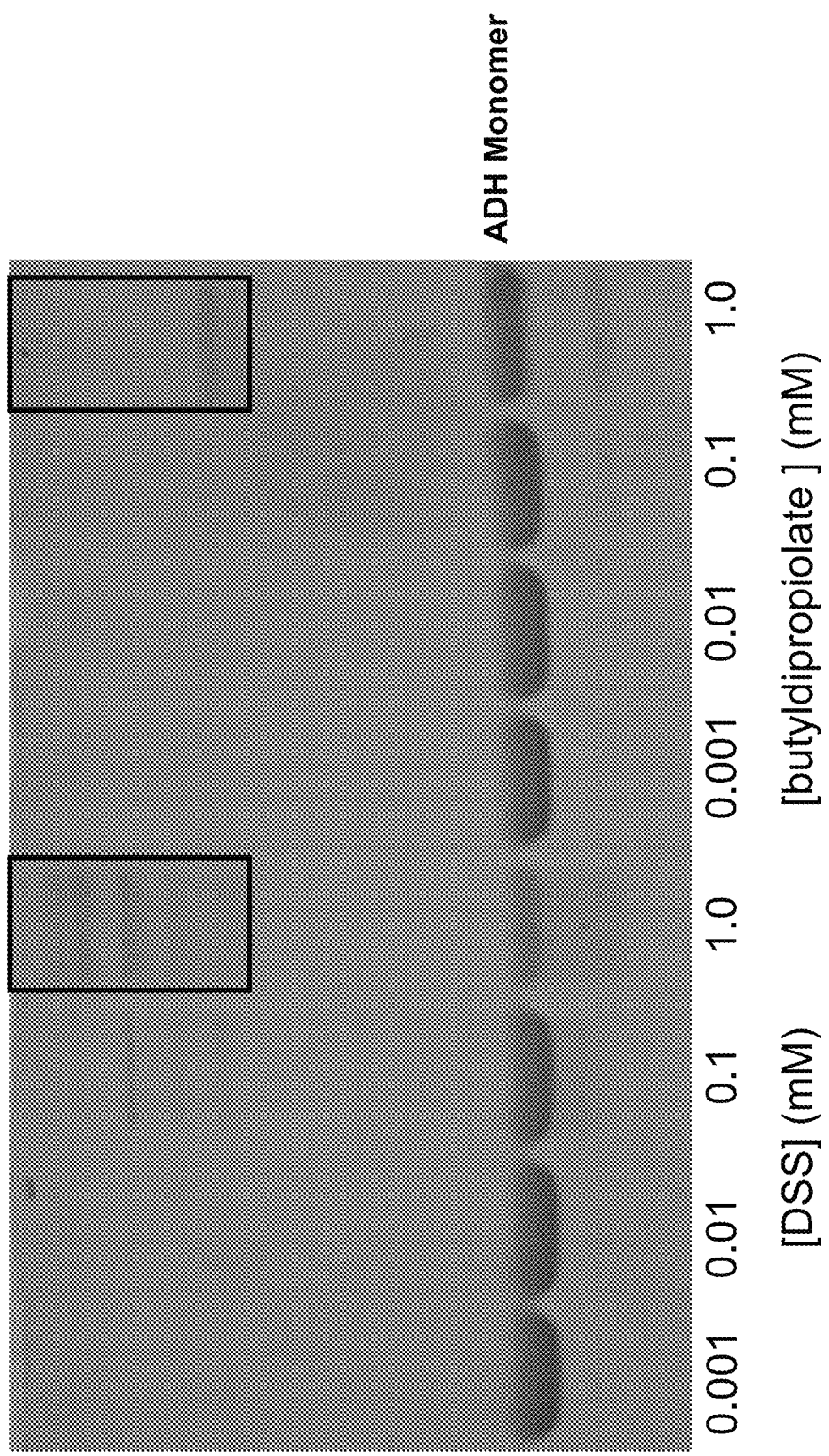
FIG. 1a is a coomassie stained polyacrylamide gel showing evidence of crosslinked yeast ADH and characteristic shifts in electrophoretic protein migration.
Figure 1B:
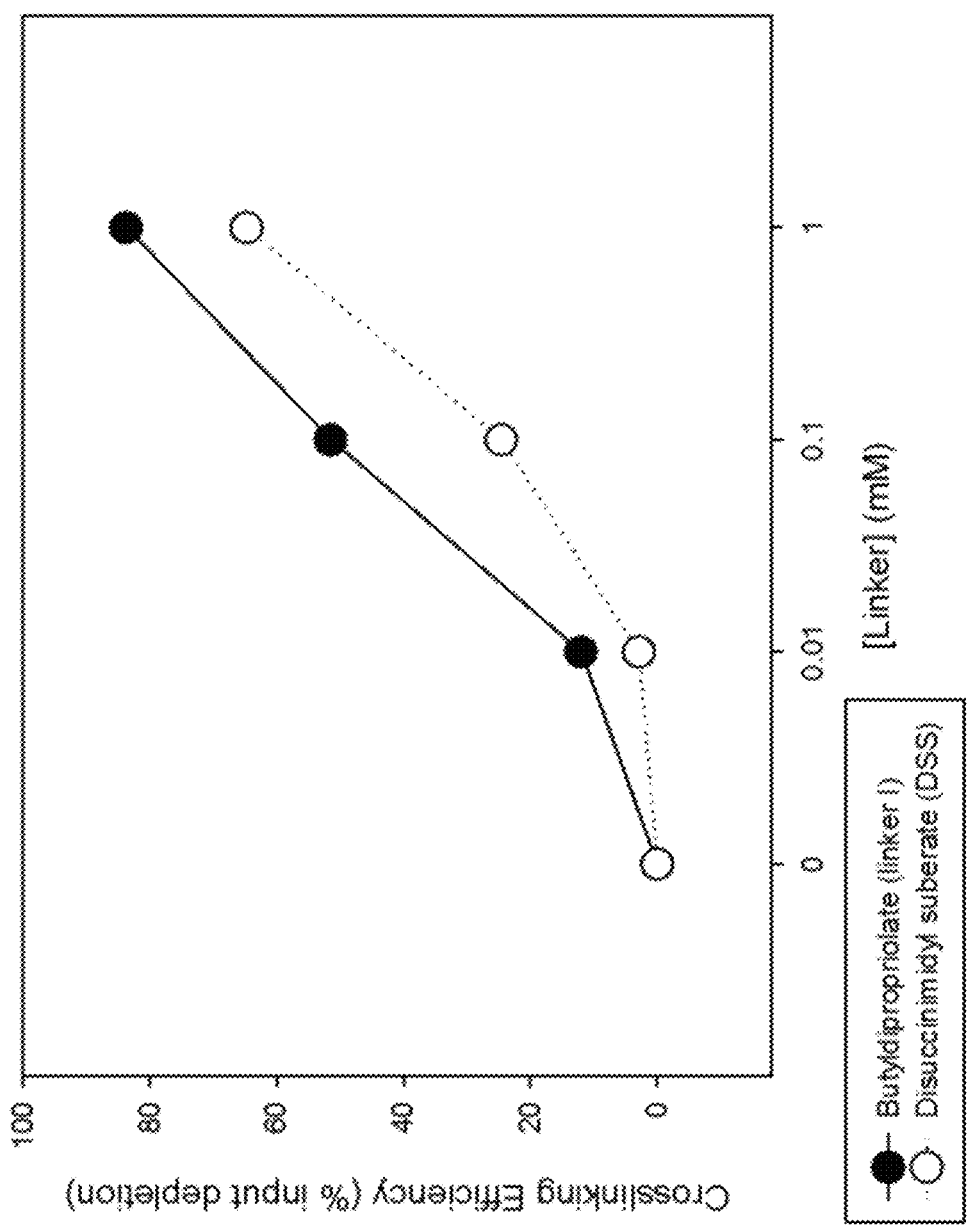
FIG. 1b is a graphical representation of crosslinker performance quantitated from coomassie stained band densities comparing disuccinimidyl suberate with butyldipropriolate.

To study whether electron-deficient alkyne Michael acceptors act as efficient amine-reactive protein crosslinkers, the inventors used a highly purified homotetrameric protein complex (ADH) as a test system for the utility of novel Michael acceptors in stabilizing protein:protein interactions via covalent coupling of accessible ε-amino groups on proximal lysine residues. ADH exists under non-denaturing conditions as a stable homotetramer, but following solubilization in chaotropic buffers (such as SDS in excess of 1%), the complex dissociates into linear monomers. ADH complexes incubated with 1 mM butyldipropiolate, then quenched with 10 mM ethanolamine showed patterns of migration with 10% SDS-PAGE indicative of molecular weight shifts consistent with the covalent coupling of dimeric proteins (FIG. 1a, black boxes). Varying the concentration of crosslinker within the preparation and keeping the DMSO % constant showed a highly concentration-dependent effect of crosslinker performance, with minimal protein crosslinking present at concentrations below 100 μM (FIG. 1b). The performance of butyldipropiolate was comparable to that of the commercial standard NHS-ester protein crosslinker DSS in terms of ½-maximal concentration. ADH should never exist under native conditions as anything more massive than a tetramer of 146 kDa in total mass, however, DSS produces a very apparent "ladder" of crosslinked ADH (FIG. 1; arrows), indicating substantial protein polymerization that reflects relatively high nonspecific crosslinking of proteins in solution. Gel bands were excised to isolate the apparent protein dimers from both DSS-crosslinked and butyldipropiolate-crosslinked gels, and used for in-gel digestion and mass spectrometry to sequence the crosslinked peptides and assign some distance parameters based on the identification of crosslinks between the peptide chains. Interrogation of the peptide chains observed to be crosslinked by butyldipropiolate indicates the crosslinks identified by StavroX can be mapped onto existing crystal structures, which shows that butyldipropiolate produces reliable crosslinks between adjacent peptide chains in ADH. This example confirms that effective protein crosslinks are created through direct coupling of ε-amino groups on proximal lysine residues, similar to NHS-ester based crosslinkers like DSS.

Example 2 pH Sensitivity

Figure 2A:
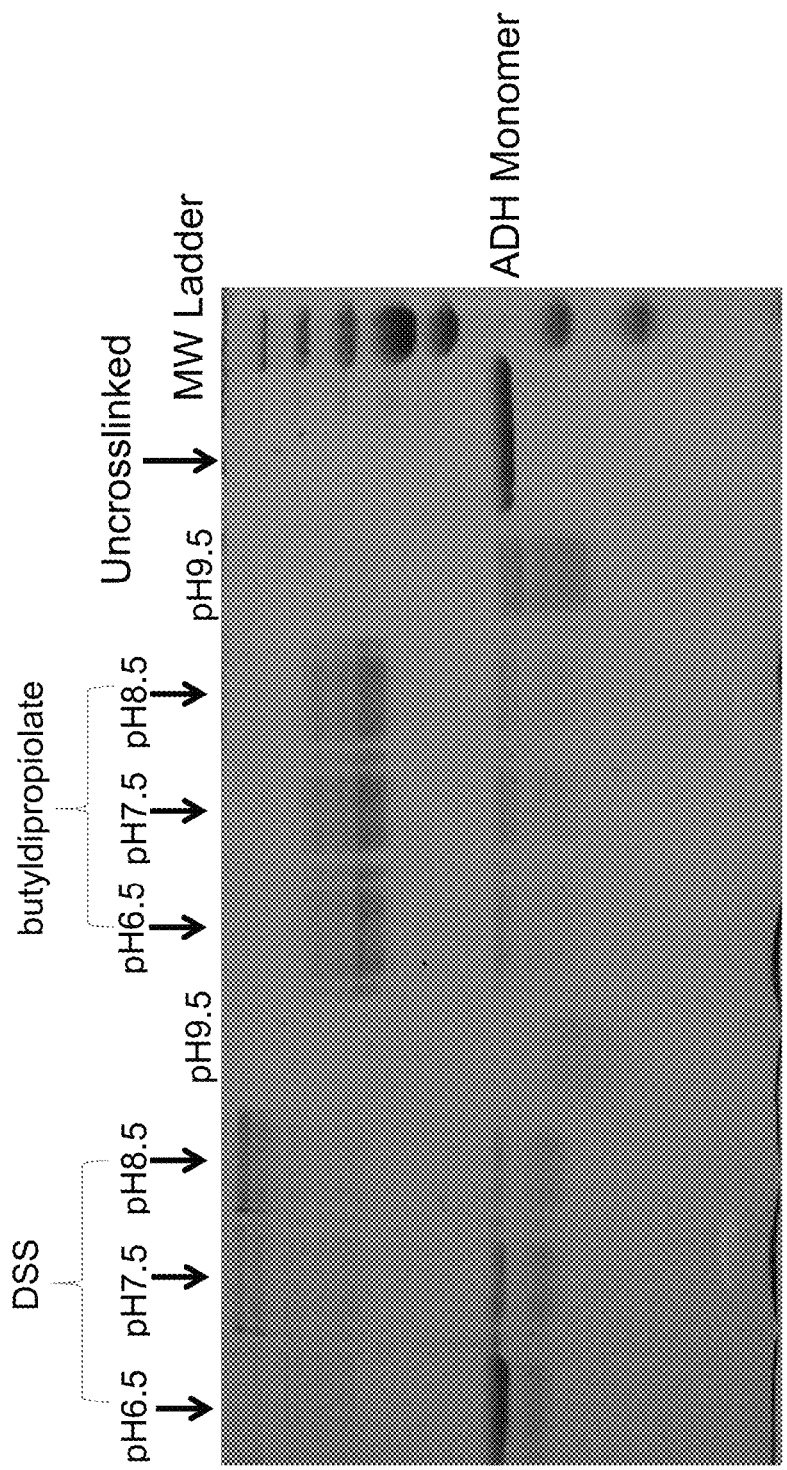
FIG. 2a is a coomassie stained polyacrylamide gel showing changes in yeast ADH protein electrophoretic mobility following crosslinking with butyldipropriolate or disuccinimidyl suberate at various pH.
Figure 2B:
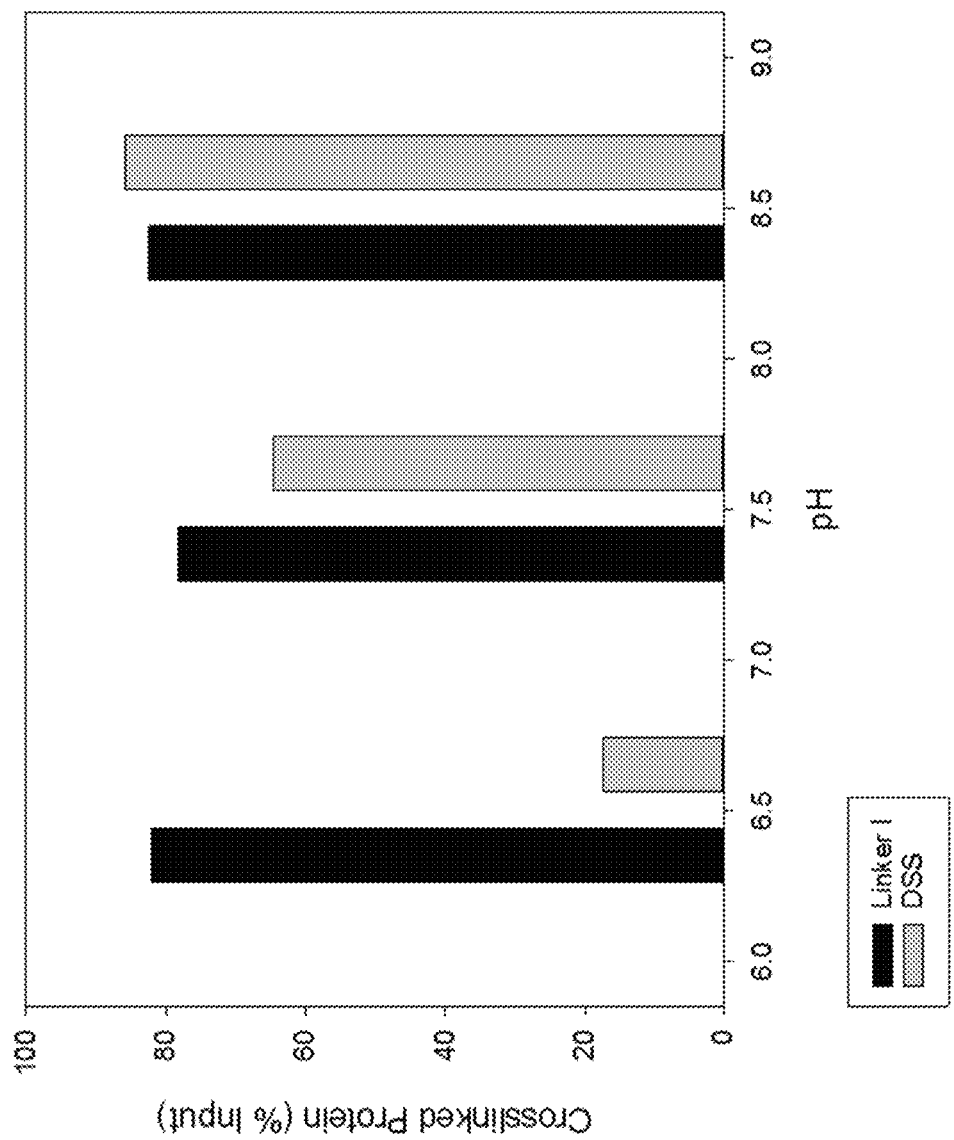
FIG. 2b is a graphical representation of crosslinker performance at different pH quantitated by coomassie band density.

NHS-ester protein reactive groups have been shown to be highly dependent on reaction buffer pH, and most commercial preparations suggest pH<8.0 for efficient reactions with ε-amines of lysine, since the deprotonated form is more likely to participate in the SN2 reaction with NHS. Because the use of Michael acceptor reactive groups may be less sensitive to variations in pH within a physiological range (6-8), the inventors used PBS at pH 6.5, 7.5, 8.5, 9.5 to probe the performance of DSS versus butyldipropiolate in cross-linking ADH across a 4-log pH range. The inventors observed ADH was crosslinked with equivalent efficiency at pH 6.5, 7.5, and 8.5, with no apparent protein observed on the gel at pH<9, indicating a nonspecific effect of very high pH on crosslinking efficiency for both DSS and butyldipropiolate (FIG. 2a, black boxes). DSS, by contrast, showed very high sensitivity to pH, with a linear decline in crosslinking efficiency observed from pH 8.5 to pH 6.5 (FIG. 2b).

When the crosslinker efficiency is substantially reduced in acidic pH relative to alkaline, as is the case with known NHS-ester linking compounds, identifying protein:protein interactions will be systematically biased towards some compartments and eliminated for others, drastically limiting the physiological relevance of any large-scale interactome analysis that depends on stabilizing transient interactions. This example shows that the Michael acceptor crosslinking compounds of this disclosure are less dependent on alkaline pH than NHS-ester crosslinkers (like DSS) and therefore are more likely to preserve relevant protein:protein interactions across cellular compartments and organelle environments that may be selected against profiling with other commercially available reagents.

Example 3 Crosslinking Specificity

Because the inventors observed very little protein "laddering" with butyldipropiolate crosslinking of ADH in solution compared to equivalent concentrations of DSS, the inventors decided to evaluate the nonspecific crosslinking between the two compounds using equimolar mixtures of ADH (protein tetramer) with BSA (protein monomer) and crosslinking under the conditions established with previous experiments. After crosslinking with either DSS or butyldipropiolate at 1 mM in PBS pH 7.4, 10% DMSO, SDS-PAGE showed very obvious nonspecific crosslinking of BSA and ADH with DSS in dose-dependent fashion (FIG. 3, insert box "a") and very little with butyldipropiolate (FIG. 3 insert box "b"). Analysis of crosslinked peptides with LC-MS/MS from excised gel bands (indicated by arrows in FIG. 3), shows that with ADH and BSA mixtures crosslinked with DSS, 9 out of 10 top-scoring crosslinked peptides reflect nonspecific crosslinking, either linking BSA to BSA, or ADH to BSA. With ADH and BSA mixtures crosslinked with butyldipropiolate, only 3 out of 10 top-scoring crosslinked peptides reflected nonspecific reactions (Table 1a) as opposed to DSS, where 9 out of 10 identified protein crosslinks indicated nonspecific reactivity between non-meaningful interactions (Table 1 b).

TABLE 1a

Identified DSS Crosslinks

| Score | m/z. | z | Mass meas. | Mass calc. | Dev(pp... | Peptide(1) | Protein(1) |
|---|---|---|---|---|---|---|---|
| 99 | 778.414 | +2 | 1555.82 | 1555.816 | 2.88 | [GKY] | >sp|P02769|ALB... |
| 86 | 581.627 | +3 | 1742.866 | 1742.864 | 1.57 | [GKYLY] | >sp|P02769|ALB... |
| 86 | 581.627 | +3 | 1742.866 | 1742.864 | 1.57 | [GKYLY] | >sp|P02769|ALB... |
| 48 | 655.997 | +3 | 1995.977 | 1995.981 | −2.12 | (mKWVTF] | >sp|P02769|ALB... |
| 44 | 633.986 | +3 | 1899.943 | 1899.941 | 1.31 | [SQY] | >sp|P02769|ALB... |
| 43 | 778.414 | +2 | 1555.82 | 1555.816 | 2.88 | [WGKY] | >sp|P02769|ALB... |
| 42 | 633.986 | +3 | 1899.943 | 1899.941 | 1.31 | [SQY] | >sp|P02769|ALB... |
| 25 | 633.986 | +3 | 1899.942 | 1899.941 | 0.64 | [SQY] | >sp|P02769|ALB... |
| 25 | 633.986 | +3 | 1899.942 | 1899.941 | 0.64 | [SQY] | >sp|P02769|ALB... |
| 21 | 851.715 | +3 | 2553.13 | 2553.128 | 0.89 | [AKAmGY] | >sp|P00330|AD... |

| Score | From)... | To(1) | Peptide(2) | Protein(2) | From(... | To(2) |
|---|---|---|---|---|---|---|
| 99 | 159 | 161 | [KADEKK... | >sp|P02769|ALB... | 151 | 158 |
| 86 | 159 | 163 | [ESHGKL... | >sp|P00330|AD... | 14 | 21 |
| 86 | 159 | 163 | [ESHGKL... | >sp|P00330|AD... | 14 | 21 |
| 48 | 0 | 6 | {YAPELLYY | >sp|P02769|ALB... | 173 | 180 |
| 44 | 52 | 54 | {mSIPET... | >sp|P00330|AD... | 0 | 12 |
| 43 | 158 | 161 | [KADEKKF} | >sp|P02769|ALB... | 151 | 157 |
| 42 | 52 | 54 | {mSIPET... | >sp|P00330|AD... | 0 | 12 |
| 25 | 52 | 54 | {mSIPET... | >sp|P00330|AD... | 0 | 12 |
| 25 | 52 | 54 | {mSIPET... | >sp|P00330|AD... | 0 | 12 |
| 21 | 191 | 196 | [AGIKWL... | >sp|P00330|AD... | 89 | 103 |

TABLE 1b

Identified butyldipropriolate Crosslinks

| Score | m/z. | z | Mass meas. | Mass calc. | Dev(pp... | Peptide(1) | Protein(1) |
|---|---|---|---|---|---|---|---|
| 29 | 711.684 | +3 | 2133.038 | 2133.043 | −2.33 | [KIGDY] | >sp|P00330|AD... |
| 29 | 835.745 | +3 | 2505.222 | 2505.222 | −0.09 | [ESHGKL... | >sp|P00330|AD... |
| 29 | 835.745 | +3 | 2505.222 | 2505.222 | −0.09 | [ESHGKL... | >sp|P00330|AD... |
| 29 | 835.745 | +3 | 2505.222 | 2505.222 | −0.09 | [ESHGKL... | >sp|P00330|AD... |
| 21 | 922.708 | +4 | 3687.811 | 3687.811 | −0.09 | [ANKYNG... | >sp|P02769|ALB... |
| 20 | 627.061 | +4 | 2505.221 | 2505.222 | −0.47 | [ESHGKL... | >sp|P00330|AD... |
| 20 | 627.061 | +4 | 2505.221 | 2505.222 | −0.47 | [ESHGKL... | >sp|P00330|AD... |
| 20 | 627.061 | +4 | 2505.221 | 2505.222 | −0.47 | [ESHGKL... | >sp|P00330|AD... |
| 20 | 627.061 | +4 | 2505.221 | 2505.222 | −0.47 | [ESHGKL... | >sp|P00330|AD... |
| 18 | 1155.31 | +4 | 4618.218 | 4618.223 | −1.11 | [JDLGEE... | >sp|P02769|ALB... |

| Score | From)... | To(1) | Peptide(2) | Protein(2) |
|---|---|---|---|---|
| 29 | 84 | 88 | [APELLYY... | >sp|P02769|ALB... |
| 29 | 14 | 21 | {MSIPET... | >sp|P00330|AD... |
| 29 | 14 | 21 | {MSIPET... | >sp|P00330|AD... |
| 29 | 14 | 21 | {MSIPET... | >sp|P00330|AD... |
| 21 | 181 | 188 | [DKLKHL... | >sp|P02769|ALB... |
| 20 | 14 | 21 | {MSIPET... | >sp|P00330|AD... |
| 20 | 14 | 21 | {MSIPET... | >sp|P00330|AD... |
| 20 | 14 | 21 | {MSIPET... | >sp|P00330|AD... |
| 20 | 14 | 21 | {MSIPET... | >sp|P00330|AD... |
| 18 | 36 | 51 | [KIGDYAG.. | >sp|P00330|AD... |

These results point to a unique property of protein crosslinking via rapid Michael addition using electron-deficient alkynes as Michael acceptor groups for protein conjugation, and this example demonstrates the use of electron-deficient alkyne crosslinking compounds of this disclosure similar to NHS-ester based crosslinkers, but with substantially reduced nonspecific protein conjugation.

Example 4 Analysis of Heteromeric Protein Interactions

The inventor next investigated whether the superior performance of butyldipropiolate could be used to explore sites of interaction between purified heteromeric protein complexes. The inventors employed a purified Skp1-Skp2 (Uniprot P63208/Q13309), which forms part of the SCF E3-ubiquitin ligase complex. This complex represented a particularly salient application of protein crosslinking and mass spectrometry-based interaction identification, as Skp1 possesses a disordered C-terminal region that is not part of any current high-resolution structural profiles. The inventors were able to successfully identify two sites of interaction between proximal lysine residues on Skp1 and Skp2, including a crosslink between the C-terminal lysine of Skp1 that appears to participate in a relevant interaction geometry with Skp2 that has not been previously described.

Profiling the structural determinants of these functionally relevant interactions with "gold standard" techniques such as electron microscopy and NMR is difficult when the target protein contains intrinsically disordered regions, such as in this Skp1-Skp2 model previously studied. The C-terminus of the S-phase kinase associated protein (Skp1) contains such a disordered region, and with crosslinker compounds of this disclosure, the inventors were able to demonstrate that a disordered region previously inaccessible to other techniques was contributing to a stable interaction with its requisite partner, Skp2. Thus, this example demonstrates the superior utility of the crosslinker compounds of this disclosure in elucidating intramolecular and intermolecular protein interactions.

Example 5 Crosslinker Variations

The previous experiments established the utility of the novel electron-deficient alkyne reactive groups of the crosslinking compounds of this disclosure to participate in Michael addition to free amines on lysine residues of purified proteins. The inventors next sought to explore the effects of alterations to the structural rigidity and length of the alkyl chain connecting the two reactive groups. Expanding the length of the chain and decreasing the hydrophobicity by replacing the 1-4-butanediol with an expanded polyethylene glycol (PEG), resulted in oxytris(ethane-2,1 diyl) dipropriolate. Increasing structural rigidity and maintaining hydrophobicity by using a dicyclohexane linker produced di(cylcohexyl-2,1-diyl) dipropriolate. In vitro crosslinking of ADH with butyldipropiolate, oxytris(ethane-2,1 diyl) dipropriolate, and di(cylcohexyl-2,1-diyl) dipropriolate, with subsequent analysis of apparent migration shifts with SDS-PAGE (FIG. 4) indicated that concentration-dependent crosslinking performance was slightly reduced for oxytris (ethane-2,1 diyl) dipropriolate, and more severely attenuated for di(cylcohexyl-2,1-diyl) dipropriolate in comparison to the prototype molecule (butyldipropiolate).

Example 6 In Vivo Crosslinking

An important application for protein crosslinker reagents is their use in the preservation and subsequent profiling of protein complexes participating in dynamic cell signaling events within living cells. The inventors used a derivative of B35 rat neuroblastoma cell line (LTR1-1d) that stably expresses α4β2 nAChRs (the major neuronal subtype) to crosslink these low-abundance protein complexes in their native environment. The α4β2 nAChR is a heteropentameric ligand-gated ion channel complex, which is assembled in alternate stoichiometries (α4(2)β2(3) and α4(3)β2(2)) to form receptors of high- and low-sensitivity to agonist activation, respectively (Zhou et al, J Neurosci 23(27):9004-15; PMID 14534234; others). Functional parameters of nAChR activation and desensitization have been interrogated for decades using electrophysiological methods and many attempts at high-resolution structural profiling of α4β2 nAChRs fail due to the exceptionally large (270 amino acids) intracellular domain between transmembrane domains 3 and 4 (hereafter referred to as the M3-M4 loop), which is predicted from informatics screens to be intrinsically disordered. (FIG. 5). The inventors used a PDB crystal structure of the Torpedo nicotinic acetylcholine receptor, used as a proxy for the α4β2 nicotinic receptor (no structure available) to aid in the visualization of approximate locations of inter-subunit crosslinks produced by incubation of live cells with butyldipropriolate and subsequent receptor purification and analysis with LC-MS/MS. The inventors used an immobilized mAb299 to immunopurify crosslinked α4β2 nAChRs from LTR1-1d cells and interrogate sites of interaction between subunits in the pentamer using mass spectrometry. This experiment represents the first successful application of crosslinking mass spectrometry used to profile sites of physical interaction between neuronal nAChR subunits. The inventors identified a number of high-confidence crosslinked peptides (Table 2a), indicating interactions between various regions of the α4 and β2 subunits. Importantly, the inventors observed two inter-subunit crosslinks occurring between α4 and β2 in the large N-terminus and in the entrance to the "vestibule" of the M3-M4 loop that occupies the region close to the transmembrane domain (where the peptides exit the lipid bilayer) (FIG. 8, red circles). This finding represents evidence that the large intracellular loop regions may closely associate in proximity to the plasma membrane and play a role in dynamic gating of the channel upon binding ligand. This example demonstrates the utility of the crosslinking compounds of this disclosure for the interrogation and elucidation of specific geometries of interaction between adjacent intramolecular protein structures.

TABLE 2a crosslinked peptides of the α4 and β2 subunits

| Linked Residues | nAChR Subunit |
| --- | --- |
| K190-K44 | α4-α4 |
| K160-K110 | α4-β2 |
| K180-K110 | α4-β2 |
| K361-K342 | α4-β2 |
| K361-K451 | α4-β2 |

Example 6 Conformational Changes Following Persistent Nicotine Exposure

Nicotinic receptors rapidly desensitize following prolonged exposure to agonist. This functional desensitization is thought to occur with corresponding changes in the conformation of the receptor, and α4β2 nAChRs are particularly prone to long-lasting periods of functional deactivation following desensitization by continuous agonist application (Marks et al, J Neurochem 63(6):2125-35; PMID 7964732; others). The inventors exposed LTR1-1d cells to nicotine for 24 hours and performed in vivo crosslinking with butyldipropiolate as described previously to probe any changes in receptor subunit interactions that may have occurred as a result of conformational changes associated with persistent nicotine exposure and desensitization. The inventors observed differential crosslinking of receptor subunits following incubation with nicotine compared to those observed under control conditions (Table 2b). These findings indicate that substantial shifts in the conformation of α4β2 nAChRs occur when ligand is bound that can be observed following crosslinking of proximal lysine residues. Conformational changes in the receptor following prolonged agonist occupation when the receptor resides in the lumen of the endoplasmic reticulum may also facilitate the binding of interacting proteins that can influence the rate of receptor assembly and/or transport of nascent receptors (Srinivassan et al, J Gen Physiol 137(1):59-79; PMID 21187334; others). This example demonstrates the utility of the crosslinking compounds of this disclosure for investigating and identifying dynamic cell signaling events such as agonist-induced desensitization.

TABLE 2b crosslinked peptides following incubation with nicotine

| Linked Residues | nAChR Subunit |
|---|---|
| K44-K95 | β2-β2 |
| K99-K103 | α4-β2 |
| K142-K103 | α4-β2 |
| K160-K110 | α4-β2 |
| K180-K110 | α4-β2 |
| K451-K590 | α4-β2 |

While the present invention has been illustrated and described with reference to certain exemplary embodiments, those of ordinary skill in the art will understand that various modifications and changes may be made to the described embodiments without departing from the spirit and scope of the present invention, as defined in the following claims.

The invention claimed is:

1. A method of cross-linking at least one of a protein, a peptide, and a nucleic acid comprising:
   mixing a composition comprising the at least one of the protein, the peptide, and the nucleic acid with a crosslinker compound having a chemical structure:

$$Z-Y-A_n-Y-Z$$

wherein:
   n is an integer between 1 and 5;
   A is an atom or a compound;
   each Z is a Michael acceptor independently selected from the group consisting of a propiolate, a propiolamide, a ynone, a ynethiolate, an acrylate, and a vinylsulfone; and,
   each Y is optional and is independently an organic compound optionally substituted with one or more heteroatoms selected from the group consisting of O, N, S, or P to form a crosslinked sample;
   fragmenting the crosslinked sample to form crosslinked fragments; and
   detecting a mass-to-charge ratio of the crosslinked fragments.

2. The method of claim 1, wherein the composition further comprises at least one of a cell lysate, a cell culture, and a tissue sample.

3. The method of claim 1, wherein the mixing step is conducted at a pH between pH 5 and pH 10.

4. The method of claim 1, further comprising purifying the crosslinked sample.

5. The method of claim 1, further comprising isolating the crosslinked fragments.

6. The method of claim 1, wherein the fragmenting step comprises digesting the crosslinked sample with an enzymatic cleaving agent or a chemical cleaving agent.

7. The method of claim 6, wherein the digesting comprises contacting the crosslinked sample with at least one of CNBr at pH 2, trypsin, Glu-C endoproteinase, pepsin, restriction nuclease enzymes, DNase I, RNase α-sarcin, and combinations thereof.

8. The method of claim 1, wherein the crosslinker compound comprises at least one collision-induced dissociation group and the method further comprises dissociating at least one of the crosslinked sample and the crosslinked fragments to form a dissociated sample.

9. The method of claim 8, wherein the dissociating comprises collisions with at least one of an inert gas, a surface, photons, thermal/black body infrared radiation, and an electron beam.

10. The method of claim 1, further comprising ionizing at least one of the crosslinked sample and the crosslinked fragments to form an ionized fragment.

11. The method of claim 10, wherein the ionizing comprises at least one of electrospray ionization (ESI), matrix-assisted laser desorption ionization (MALDI), and fast atom bombardment (FAB).

12. The method of claim 1, wherein the detecting step comprises:
    directing the crosslinked fragments through a first mass resolving spectrometer to select precursor ions having a first desired mass-to-charge ratio;
    subjecting the precursor ions to dissociation to form product ions having a second mass-to-charge ratio; and
    detecting the product ions.

13. The method of claim 1, wherein A is selected from the group consisting of a $C_{1-10}$ alkyl, a cycloalkyl, a heteroalkyl, and a heterocycloalkyl, wherein when A is the heteroalkyl or the heterocycloalkyl, the heteroatom is selected from at least one of phosphorus (P), sulfur (S), nitrogen (N), or oxygen (O).

14. The method of claim 1, wherein each Michael acceptor is the propiolate.

15. The method of claim 1, wherein the crosslinker compound comprises an affinity handle (Q) selected from the group consisting of:
    a) a chemical moiety that facilitates enrichment of crosslinked species from a sample;
    b) a chemical moiety that facilitates precipitation or separation of the crosslinker compound from a sample;
    c) at least one of biotin, a histidine residue, and PEG; and,
    d) at least one of an amino acid sequence, polyhistidine, an antibody fragment, and a nucleic acid sequence.

16. The method of claim 1, wherein the crosslinker compound comprises a molecular label (L) selected from the group consisting of: a phosphor, a radioactive atom, a atomic isotope, a fluorescent dye, a electron-dense reagent, an enzyme, biotin, digoxigenin, hapten, hydrolase, phosphatase, esterase, glycosidase, oxidotase, peroxidase, fluorescein or its derivatives, rhodamine or its derivatives, dansyl, umbel-liferone, luciferin, 2,3-dihydrophthalazinedione, a stable isotope, and a detectable proteins that incorporates a metal, radiolabel, or a phosphor.

17. The method of claim 1, wherein each linking group (Y) independently comprises one or more cleavage sites that is capable of being cleaved by at least one of a chemical cleavage agent, an enzymatic cleavage agent, or both chemical cleavage agents and enzymatic cleavage agents.

18. The method of claim 1, wherein each linking group (Y) comprises one or more collision-induced dissociation groups, each collision-induced dissociation group capable of forming a signature ion upon collision-induced dissociation in mass spectrometric methods.

19. The method of claim 1, wherein the crosslinker compound has a molecular length of between about 1 angstrom and about 50 angstroms.

* * * * *